(12) United States Patent
Hayes et al.

(10) Patent No.: US 10,513,568 B2
(45) Date of Patent: Dec. 24, 2019

(54) METHODS OF MAKING STABLE AND THERMALLY POLYMERIZABLE VINYL, AMINO OR OLIGOMERIC PHENOXY BENZOCYCLOBUTENE MONOMERS WITH IMPROVED CURING KINETICS

(71) Applicant: Rohm and Haas Electronic Materials LLC, Marlborough, MA (US)

(72) Inventors: Colin Hayes, Marlborough, MA (US); Michael K. Gallagher, Hopkinton, MA (US); Michelle Riener, Watertown, MA (US)

(73) Assignee: Rohm and Haas Electronic Materials, Marlborough, MA (US)

( * ) Notice: Subject to any disclaimer, the term of this patent is extended or adjusted under 35 U.S.C. 154(b) by 0 days.

(21) Appl. No.: 15/828,972

(22) Filed: Dec. 1, 2017

(65) Prior Publication Data
US 2019/0169327 A1   Jun. 6, 2019

(51) Int. Cl.
| | |
|---|---|
| *C08F 32/02* | (2006.01) |
| *C08F 12/02* | (2006.01) |
| *C08G 81/02* | (2006.01) |
| *C07C 69/01* | (2006.01) |
| *C07C 35/31* | (2006.01) |
| *C07C 23/18* | (2006.01) |
| *C08K 5/09* | (2006.01) |
| *C07C 69/017* | (2006.01) |
| *C07C 41/01* | (2006.01) |
| *C08F 12/22* | (2006.01) |
| *C08F 212/08* | (2006.01) |
| *G01N 25/48* | (2006.01) |

(52) U.S. Cl.
CPC .............. *C08F 32/02* (2013.01); *C07C 23/18* (2013.01); *C07C 35/31* (2013.01); *C07C 41/01* (2013.01); *C07C 69/017* (2013.01); *C08F 12/02* (2013.01); *C08F 12/22* (2013.01); *C08F 212/08* (2013.01); *C08G 81/025* (2013.01); *C08K 5/09* (2013.01); *G01N 25/4866* (2013.01)

(58) Field of Classification Search
CPC ........ C08F 32/02; C08F 12/02; C08G 81/025; C07C 69/017; C07C 35/31; C07C 23/18; C08K 5/09; G01N 25/4866
USPC .......................................................... 526/334
See application file for complete search history.

(56) References Cited

U.S. PATENT DOCUMENTS

| | | | |
|---|---|---|---|
| 4,783,514 A * | 11/1988 | Kirchhoff | C07C 13/44 526/281 |
| 6,361,926 B1 | 3/2002 | So et al. | |
| 7,342,053 B2 | 3/2008 | Nakamura | |
| 8,492,510 B2 | 7/2013 | Harth et al. | |
| 2014/0019393 A1 | 1/2014 | Modha | |
| 2015/0184017 A1 | 7/2015 | Hustad et al. | |
| 2015/0210793 A1* | 7/2015 | Park | C08F 212/08 524/553 |
| 2017/0081550 A1* | 3/2017 | Romer | C09D 171/02 |
| 2017/0170400 A1* | 6/2017 | Spencer | C08G 61/12 |
| 2017/0174805 A1 | 6/2017 | Romer et al. | |
| 2017/0174810 A1 | 6/2017 | Romer et al. | |

FOREIGN PATENT DOCUMENTS

| | | | |
|---|---|---|---|
| CN | 101226786 A | * | 7/2008 |
| CN | 101226786 A | | 7/2008 |
| CN | 103596360 A | | 2/2014 |
| EP | 527572 A1 | | 2/1993 |
| WO | 2013005026 A2 | | 1/2013 |
| WO | 2017031622 A1 | | 3/2017 |

OTHER PUBLICATIONS

Dobish, et al; Synthesis of Low-Temperature Benzocyclobutene Cross-Linker and Utilization; Polymer Chemistry; vol. 3; pp. 857-860; 2012.

So et al; Styrene 4-Vinylbenzocyclobutene Copolymer for Microelectronic Applications; Journal of Polymer Science: Part A: Polymer Chemistry; vol. 45; pp. 2799-2806; 2008

Hayes et al; Effect of Ring Functionalization on the Reaction Temperature of Benzocyclobutene Thermoset Polymers; Macromolecules; vol. 49; pp. 3706-3715; 2016.

Anonymous: "Maleirnidocyclobutaraene monomers", Research Disclosure, Aug. 1, 1992, vol. 340, No. 118.

Search report for corresponding European Application No. 18 20 9684 dated Apr. 5, 2019.

* cited by examiner

*Primary Examiner* — Michael Bernshteyn
(74) *Attorney, Agent, or Firm* — S. Matthew Cairns

(57) ABSTRACT

The present invention provides methods of making low energy polymerizable monomers and resins for use in making dielectric materials. The methods comprise deprotecting or deacylating an organic alkali cleavable protecting group containing addition polymerizable, amine containing aromatic monomer or oligoaromatic phenol resin containing an organic alkali cleavable protecting group, such as a $C_2$ to $C_9$ alkanoyl group, preferably, an acyl group, by hydrolyzing to remove the protecting group in organic alkali in a polar solvent containing an excess of alkali $C_1$ to $C_7$ alkoxide and form a hydroxyl functional monomer or resin, followed by; reacting via nucleophilic substitution the resulting hydroxyl functional monomer or resin with an alpha-halide (α-halide) or strong acid conjugate leaving group containing arylcyclobutene compound in a polar solvent, to yield a product an arylcyclobutene-containing addition polymerizable or amine containing aromatic monomer or oligoaromatic phenol resin having an ether linkage from the cyclobutene ring to an aromatic group of the addition polymerizable aromatic monomer, aromatic amine or oligoaromatic phenol.

10 Claims, No Drawings

METHODS OF MAKING STABLE AND THERMALLY POLYMERIZABLE VINYL, AMINO OR OLIGOMERIC PHENOXY BENZOCYCLOBUTENE MONOMERS WITH IMPROVED CURING KINETICS

The present invention relates generally to methods of making monomer materials, and, more particularly, to methods of making addition polymerizable, aromatic amine or oligoaromatic phenol arylcyclobutene-containing monomers or resins having one or more aryloxy, such as phenoxy, or oligophenolic groups comprising reacting an alpha-halide (α-halide) or strong acid conjugate leaving group, such as a sulfonate leaving group, for example, an o-tosyl or triflate leaving group, containing arylcyclobutene compound, such as a 1-bromo benzocyclobutene (α-Br BCB), with an hydroxyl functional aromatic monomer or oligoaromatic resin containing an addition polymerizable group, containing an amine group, or an oligoaromatic resin containing one or more phenol ring or phenolic hydroxyl group. The hydroxyl functional aromatic monomer or oligoaromatic resin is formed by deprotecting it in organic alkali and a polar solvent to remove an organic alkali cleavable protecting group from a protecting group containing aromatic monomer or oligoaromatic resin.

Vinyl benzocyclobutene (vinyl BCB) styrenic copolymers provide many of the dielectric benefits known BCB containing dielectrics at a significantly reduced cost. However, unsubstituted BCB monomers require a 250° C. temperature for 1 hour for cure, which renders them unsuitable for use with many polymer or plastic materials. Substitution of the BCB ring can afford reduced cure temperatures, but often requires several additional synthetic steps and often results in low monomer yields (<70%) in unstable monomer compounds. For example, known alkoxy substituted BCBs do not survive thermal radical polymerizations due to ring opening polymerization of the BCB and so are unsuitable for applications which require orthogonal cure among addition and ring opening.

Previously, Harth et al. in "Synthesis of low-temperature cross-linker and utilization," *Polymer Chemistry*, 2012, 3(4), at 857-860, teaches of a 1-substituted alkoxy BCB having the alkoxy group on the cyclobutene ring, which is grafted to a poly(acrylic acid) post-polymerization to impart a low temperature cure property for the BCB groups. Recent experiments produced a 1-alkoxy methacrylate BCB and isolated the monomer through use of an expensive silver catalyst; however, the material was unstable at 80° C. where conventional free radical polymerizations are carried out leading to a styrenic polymer that is highly crosslinked and not further curable through a Diels Alder cycloaddition.

Further, aliphatic alkoxy BCBs are thermally processed at too low a temperature for many applications, such as spin coating on a wafer and subsequent removal of the solvent owing to the high boiling point of solvents required for safe operation in semiconductor fabrication. Such aliphatic alkoxy linkages are known to lower ring opening thereby disabling the orthogonal Diels Alder reaction.

The present inventors have sought to solve the problem of providing a simple method for making a stable addition polymerizable BCB monomer useful for making a dielectric material that enables the provision of addition polymerized and ring opening cured (co)polybenzocyclobutenes having a low dielectric constant and low dielectric loss.

STATEMENT OF THE INVENTION

In accordance with a first aspect of the present invention, a method of making a monomer or resin composition comprises deprotecting or deacylating an addition polymerizable or amine containing aromatic monomer or an oligoaromatic resin containing an organic alkali cleavable protecting group, such as a $C_2$ to $C_9$ alkanoyl group, preferably, an acyl group; or an alkyl carbonate group, such as methyl carbonate, preferably, the monomer or resin being an addition polymerizable group containing monomer, or, more preferably, an acetoxystyrene, by hydrolyzing to remove the organic alkali cleavable protecting group in organic alkali and a polar solvent containing an excess of alkali $C_1$ to $C_7$ alkoxide, preferably, alkali $C_1$ to $C_4$ alkoxide or, more preferably, sodium methoxide to form an hydroxyl functional addition polymerizable aromatic monomer, such as 4-vinyl phenol or 4-vinyl napthol; a hydroxyl functional aromatic amine containing monomer, for example, 4-aminophenol; or an oligoaromatic phenol compound containing one or more phenolic hydroxyl, such as a phenolic novolac or resole; preferably, a hydroxystyrene, followed by; reacting via nucleophilic substitution the resulting hydroxyl functional addition polymerizable aromatic monomer, hydroxyl functional aromatic amine functional group containing monomer or hydroxyl functional oligoaromatic compound with an alpha-halide (α-halide) or strong acid conjugate leaving group containing arylcyclobutene compound, preferably, having a bromide, on the cyclobutene ring, or, more preferably, a 1-bromo benzocyclobutene (α Br BCB), in a polar solvent, such as a polar protic solvent, such as an alkanol or alkanone, or polar aprotic solvent, such as an ether, an alkyl ester or amide, preferably, a non-aqueous solvent or anhydrous solvent, to yield a product arylcyclobutene-containing addition polymerizable monomer, aromatic amine functional group monomer or oligoaromatic phenol having an ether linkage from the cyclobutene ring to an aromatic group of the addition polymerizable aromatic monomer, aromatic amine or oligoaromatic phenol, preferably, an oligoaromatic phenol resin containing from one to six, more preferably, from two to four, arylcyclobutene groups.

In accordance with the methods of making a monomer or resin composition of the first aspect of the present invention, the reacting via nucleophilic substitution comprises heating the hydroxyl functional addition polymerizable aromatic monomer, hydroxyl functional aromatic amine containing monomer or hydroxyl functional oligoaromatic compound with the alpha-halide (α-halide) or strong acid conjugate leaving group containing arylcyclobutene compound in an organic alkali and polar solvent to from 55 to 80° C., or, preferably, from 60 to 75° C., preferably, in the presence of a free radical inhibitor.

In accordance with methods of making a monomer or resin composition of the first aspect of the present invention, the hydroxyl functional addition polymerizable aromatic monomer, hydroxyl functional aromatic amine containing monomer or hydroxyl functional oligoaromatic compound formed by deprotecting or deacylating comprises a hydroxyl functional addition polymerizable aromatic monomer chosen from a styrene alcohol; a vinylphenol; an allyl phenol; an alkynyl phenol; a vinyl naphthol; a vinyl oligophenol; a vinylphenol having multiple vinyl groups, preferably, 2 to 6 vinyl groups; a vinylphenol having multiple vinyl groups and multiple aromatic rings, such as from 2 to 20 aromatic rings, or, preferably, from 2 to 6 of each of vinyl groups and aromatic rings; an allyloligophenol having from 2 to 20, or, preferably, from 2 to 6 aromatic rings or phenolic rings; an alkynyloligophenol having from 2 to 20, or, preferably, from 2 to 6 aromatic rings or phenolic rings.

In accordance with the methods of making a monomer or resin composition of the first aspect of the present invention, wherein when the hydroxyl functional addition polymerizable aromatic monomer, hydroxyl functional aromatic amine or hydroxyl functional oligoaromatic phenol formed by deprotecting or deacylating comprises a vinyl oligophenol having from 2 to 10 aromatic rings or phenolic rings, an aminophenol, an amino oligophenol or any oligoaromatic phenol, it is substantially free of aldehydes.

Preferably, the hydroxyl functional addition polymerizable aromatic monomer, hydroxyl functional aromatic amine containing monomer or hydroxyl functional oligoaromatic compound formed by deprotecting or deacylating comprises a compound of any of the formulae (1) to (9) or (D), below:

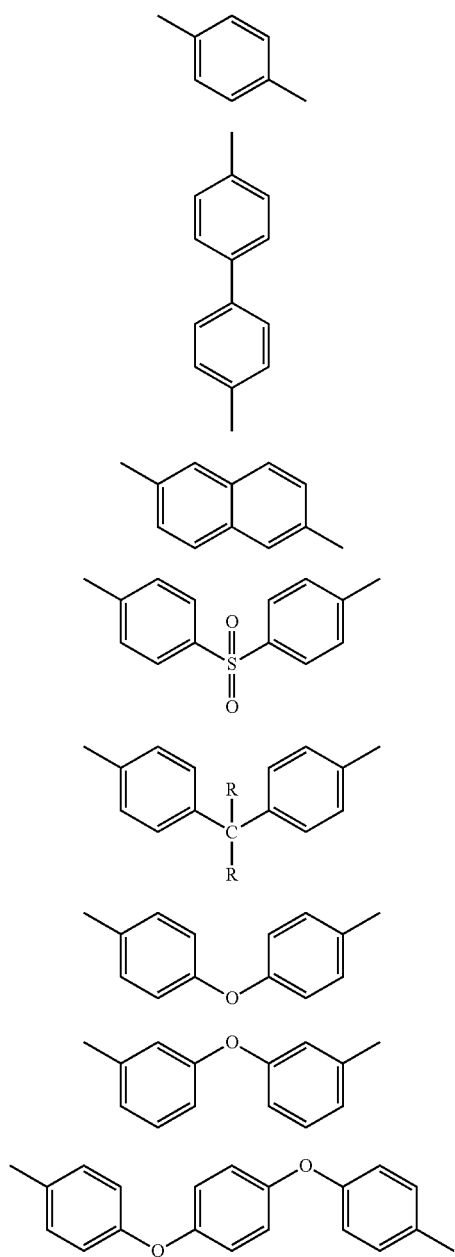

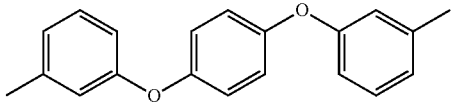

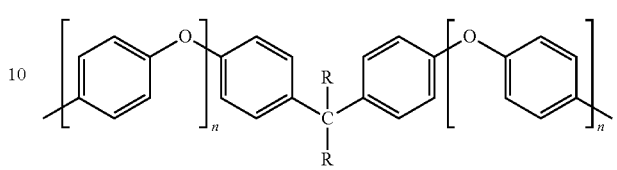

wherein R is independently any of H, $CH_3$, $CH_3CH_2$—, —$C(CH_3)_2$—, —$C(CH_3)(CH_2CH_3)$—, —$C(Ph_2)$)—, $SO_2$ or Ph-, wherein Ph is phenyl; and wherein n is an integer of from 0 to 10; and, further wherein, when the hydroxyl functional monomer or resin is a hydroxyl functional aromatic amine containing monomer, at least one aromatic ring contains an amine group.

In accordance with methods of making a monomer or resin composition of the first aspect of the present invention, wherein the organic alkali cleavable protecting group on the protecting group containing aromatic monomer or oligoaromatic resin is chosen from a $C_2$ to $C_9$ alkanoyl group, such as acyl, alkyl substituted acyl, propionyl, butyryl, pivaloyl, alkylpivaloyl, a halogenated acyl group, such as a trifluoro acyl group (other), a benzoate or an alkyl benzoate; or an alkyl carbonate, such as a methyl carbonate or a 9-fluorenylmethyl carbonate (FMoc); preferably, a $C_2$ to $C_7$ alkanoyl group, or, more preferably, an acyl or alkyl substituted acyl group.

In accordance with methods of making a monomer or resin composition of the first aspect of the present invention, the protecting group containing aromatic monomer or oligoaromatic resin having an organic alkali cleavable protecting group can be a compound of any of the formulae A1 or A2, below, wherein Ac represents an acyl or alkyl substituted acyl, and R represents any of a $C_1$ to $C_6$ divalent aliphatic hydrocarbon radical, e.g. alkylene, such as methylene, secondary and tertiary alkylenes, for example, isobutylene or tert-butylene or halogenated branched alkylenes, such as ditrifluoromethyl-substituted alkylenes; or an ether containing divalent hydrocarbon:

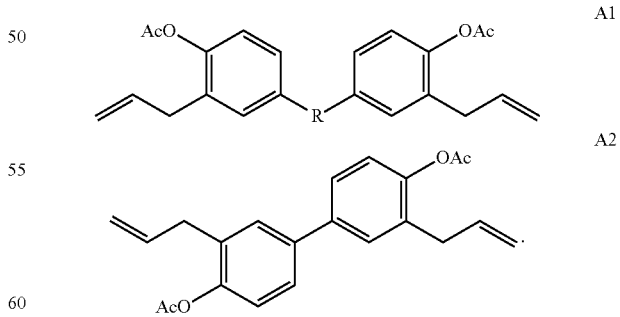

In accordance with methods of making a monomer or resin composition of the first aspect of the present invention, the methods further comprise purifying the product arylcyclobutene-containing addition polymerizable monomer, aromatic amine containing monomer or oligoaromatic phenol resin having an ether linkage from the cyclobutene ring to an aromatic group of the addition polymerizable aromatic monomer, aromatic amine or oligoaromatic phenol, such as by extracting the monomer in an aqueous polar solvent mixture, such as water and ethyl acetate, preferably, followed by removing the aqueous component by extracting it with a base, an alkali metal halide salt, or both, combining the organic residues from the monomer extract and the aqueous extraction, and then drying the combined organic residues.

In accordance with methods of making a monomer or resin composition of the first aspect of the present invention, the methods further comprise reacting the product arylcyclobutene-containing aromatic amine having an ether linkage from the cyclobutene ring to an aromatic group of the aromatic amine with an unsaturated anyhydride, preferably, maleic anhydride, in the presence of a radical inhibitor to form an aromatic maleimide of an arylcyclobutene-containing aromatic maleimide monomer having an ether linkage from the cyclobutene ring to an aromatic group of the maleimide. Alternatively, other unsaturated anhydrides can be used to generate polymerizable imides such as, itaconic anhydride, 4-ethynyl phthallic anhydride, 4-methylethynyl phthallic anhydride, and 4-phenyl ethynyl phthallic anhydride.

In accordance with a second aspect of the present invention, monomer or resin compositions comprise one or more arylcyclobutene-containing, such as a benzocyclobutene (BCB)-containing, addition polymerizable monomer, aromatic amine or oligoaromatic phenol monomer or resin having an ether linkage from the cyclobutene ring to an aromatic group of the addition polymerizable aromatic monomer, aromatic amine or oligoaromatic phenol in a purity of at least 90 wt %, or, preferably, at least 95 wt. % of the composition, preferably, as a solid.

In accordance with the monomer or resin compositions of the second aspect of the present invention, wherein the monomer is substantially free of 2-methylbenzaldehyde, as in the following formula V:

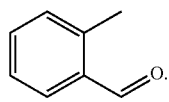
V

In accordance with the monomer or resin compositions of the second aspect of the present invention, wherein the compositions comprise from less than 10 ppm preferably, less than 1 ppm of an alkali or alkaline earth metal impurity.

In accordance with the monomer or resin compositions of the second aspect of the present invention, the arylcyclobutene-containing monomer or resin contains an addition polymerizable group, an amine group or two or more aromatic rings and is chosen from a vinyl phenoxy BCB, vinylnaphthyl BCB, an allyl phenoxy BCB, an alkynyl phenoxy BCB, a vinyl oligophenoxy BCB, an allyl oligophenoxy BCB, an aminophenoxy BCB, an amino oligophenoxy BCB, a novolac phenoxy BCB or an oligophenolic BCB.

In accordance with the monomer or resin composition of the second aspect of the present invention, the product preferably comprises an addition polymerizable group containing arylcyclobutene monomer having two vinyl groups, wherein Ar is any of the following formulae (1) to (9), below, and, wherein in the formulae (1) to (9), below, R=H, CH$_3$, CH$_3$CH$_2$—, —C(CH$_3$)$_2$—, —C(CH$_3$)(CH$_2$CH$_3$)—, —C(Ph$_2$))-, SO$_2$ or Ph-, wherein Ph is phenyl:

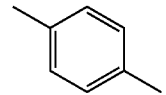
(1)

(2)

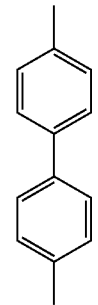
(3)

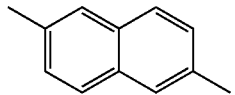
(4)

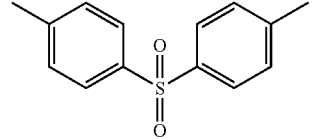
(5)

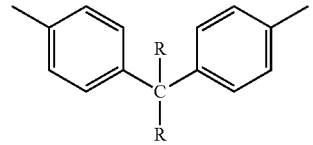
(6)

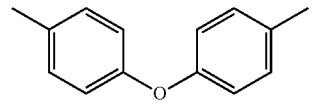
(7)

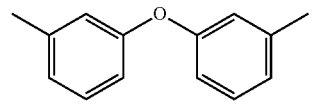
(8)

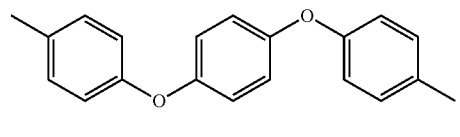
(9)

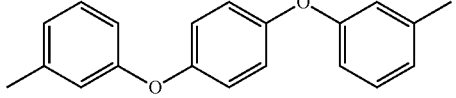

In accordance with the monomer or resin composition of the second aspect of the present invention, the product preferably comprises an arylcyclobutene containing oligoaromatic phenol resin having multiple arylcyclobutene groups of any of the following formulae (11), below:

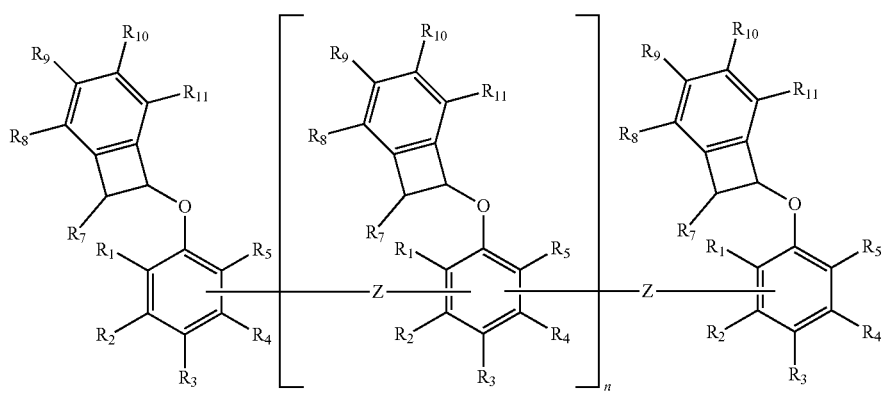

(11)

wherein, Z=—CH$_2$—, —CH$_2$—CH$_2$—, —CH$_2$—Ar—CH$_2$—, a C$_3$ to C$_4$ alkylene or an ether, n is an integer from 0 to 8, preferably 0 to 4, and each of R$_1$, R$_2$, R$_3$, R$_4$, R$_5$, R$_6$, R$_7$, R$_8$, R$_9$, R$_{10}$, and R$_{11}$, is independently H, deuterium, methyl or ethyl, preferably, H.

In accordance with the monomer or resin compositions of the second aspect of the present invention, the monomer or resin compositions comprise the arylcyclobutene-containing addition polymerizable monomer or the arylcyclobutene-containing aromatic maleimide monomer and, further, comprise an aromatic addition polymerizable monomer, such as styrene.

Unless otherwise indicated, conditions of temperature and pressure are ambient or room temperature (RT) and standard pressure. All ranges recited are inclusive and combinable.

Unless otherwise indicated, any term containing parentheses refers, alternatively, to the whole term as if no parentheses were present and the term without them, and combinations of each alternative. Thus, the term "(meth)acrylate" refers to an acrylate, a methacrylate, or mixtures thereof.

As used herein, all amounts are percent by weight and all ratios are molar ratios, unless otherwise noted.

All numerical ranges are inclusive of the endpoints and combinable in any order, except where it is clear that such numerical ranges are constrained to add up to 100%.

As used herein, the articles "a", "an" and "the" refer to the singular and the plural.

As used herein, the term "alkyl" includes linear, branched and cyclic alkyl. Likewise, "alkenyl" refers to linear, branched and cyclic alkenyl. "Aryl" refers to aromatic carbocycles and aromatic heterocycles.

As used herein, the term "aliphatic" refers to an open-chain carbon-containing moiety, such as alkyl, alkenyl and alkynyl moieties, which may be linear or branched. Also as used herein, the term "alicyclic" refers to a cyclic aliphatic moiety, such as cycloalkyl and cycloalkenyl. Such alicyclic moieties are non-aromatic, but may include one or more carbon-carbon double bonds. "Halide" refers to fluoro, chloro, bromo, and iodo. The term "(meth)acrylate" refers to both methacrylate and acrylate, and likewise the term (meth)acrylamide refers to both methacrylamide and acrylamide.

Unless the context clearly indicates otherwise, by "substituted" alkyl, alkenyl, or alkynyl is meant that one or more hydrogens on the alkyl, alkenyl or alkynyl is replaced with one or more substituents chosen from halide, hydroxy, C$_{1-10}$ alkoxy, amino, mono- or di-C$_{1-10}$ hydrocarbyl substituted amino, C$_{5-20}$ aryl, and substituted C$_{5-20}$ aryl.

Unless the context clearly indicates otherwise, by "substituted" aryl is meant that one or more hydrogens on the aryl is replaced by one or more substituents chosen from halide, hydroxy, C$_{1-10}$ alkyl, C$_{2-10}$ alkenyl, C$_{2-10}$ alkynyl, C$_{1-10}$ alkoxy, amino, mono- or di-C$_{1-10}$ hydrocarbyl substituted amino, C$_{5-20}$ aryl, and substituted C$_{5-20}$ aryl. "Alkyl" refers to an alkane radical, and includes alkane diradicals (alkylene) and higher-radicals. Likewise, the terms "alkenyl", "alkynyl" and "aryl" refer to the corresponding mono-, di- or higher-radicals of an alkene, alkyne and arene, respectively.

As used herein, the term "addition polymerizable group" means any unsaturation functional group that polymerizes via addition polymerization, including vinyl, vinylidene or allyl groups and any such group having any alkyl, alkoxy, S, N, P, O or Si heteroatom containing hydrocarbon substituent or component, or any siloxy, cyano, aryl, alkylaryl, S, N, P, O or Si heteroatom containing aryl group, carbonyl, carboxyl(ate), aldehyde, diketo, hydroxyl, amine, imine, azo, phosphorus or sulfur containing group as a substituent or component.

As used herein, the term "curing" is meant any process, such as addition crosslinking or condensation, that increases the molecular weight of a polymer material or composition through the use of the methods making or using the compositions in accordance with the present invention. "Curable" refers to any polymer material capable of being cured under certain conditions.

As used herein, the term "ASTM" refers to publications of ASTM International, West Conshohocken, Pa.

As used herein, the term "DSC" or "Differential Scanning Calorimetry" refers to a method of measuring polymer cure profiles or exotherms using a 02000™ DSC instrument (TA Instruments, New Castle, Del.). DSC was carried out using a sample of isolated uncured polymer (<5 mg) placed in a sealed Tzero™ Aluminum hermetic sample pan (TA instruments). The sample pan was then put in the DSC cell along with a control pan and the DSC was then heated from RT to 300° C. at a rate of 10° C. per minute.

As used herein, the term "formula weight" refers to the molecular weight of a representative formula depicting a given material.

As used herein, the term "hetero" or "heteroatom" when used referring to an organic group means an O, P, N, S or Si atom.

As used herein, the term "NMR" refers to nuclear magnetic resonance as determined by dissolving from 5 to 100 mg of sample material in 0.7 ml deuterated chloroform (ACROS Organics, part of Thermo Fisher Scientific, Pittsburgh, Pa.), then a spectrum was obtained on a 600 MHz instrument (Bruker BioSpin Corporation, Billerica, Mass.) or a 500 MHz instrument (Varian, Inc, Palo Alto, Calif.).

As used herein, the term "oligomer" refers to relatively low molecular weight materials such as dimers, trimers, tetramers, pentamers, hexamers, and the like that are capable of further curing or polymerization. As used herein, an "oligoaromatic phenol compound" or "oligoaromatic phenol resin" includes a phenol and one or more additional aromatic rings and may have up to 30, or, preferably, up to 10 aromatic or phenyl groups, and may be an oligophenol, such as a phenol novolac or resole.

As used herein, the term "organic alkali" means a basic reaction medium in a polar solvent including alkyl alkali, such as an alkali alkoxide. An "organic alkali" preferably does not include added water but may include up to 5,000 ppm of water formed by hydrolysis or moisture in acidic or amine containing materials.

As used herein, the term "solids" refers to any materials that remain a reaction product of the present invention; thus, solids include monomers and non-volatile additives that do not volatilize upon any of B-staging, polymerization and cure. Solids exclude water, ammonia and volatile solvents.

As used herein, the term "substantially free" of a given material means that a composition contains 1,000 ppm or less, or, preferably, 500 ppm or less of that material. As used herein, the term "anhydrous" means substantially free of water.

As used herein, unless otherwise indicated, the term "weight average molecular weight" or "Mw" means that value determined by gel permeation chromatography (GPC) of a polymer solution in tetrahydrofuran (THF) at room temperature using a Waters Alliance High Pressure Liquid Chromatogram (HPLC) (Waters, Milford, Mass.) equipped with an isocratic pump, an autosampler (Injection volume (100-150 µl) and a Series of 4 Shodex™ (8 mm×30 cm) columns, each filled with a polystyrene divinyl benzene (PS/DVB) gel against a standard calibrated from polystyrene as standards. As used herein, "number average molecular weight" or "Mn" is measured in the same way as weight average molecular weight and represents the median molecular size in a given polymer composition. As used herein, the term "PDI" refers to the ratio of Mw/Mn.

As used herein, the term "wt. %" stands for weight percent.

As used throughout this specification, the following abbreviations shall have the following meanings, unless the context clearly indicates otherwise: ° C.=degree Celsius; min.=minutes; hr.=hours; g=gram; L=liter; L m=micron=micrometer; nm=nanometer; mm=millimeter; mL=milliliter; MPa=megapascal; $M_w$=weight average molecular weight; $M_n$=number average molecular weight; AMU=atomic mass unit and ppm is part per million. Unless otherwise noted, "wt. %" refers to percent by weight, based on the total weight of a referenced composition.

In accordance with the present invention, arylcyclobutene-containing monomers or resins, such as vinyl phenoxy BCB, allyl phenoxy BCB, amino(oligo)phenol BCB, or oligoaromatic phenol BCB monomers or resins are synthesized in two steps from an arylcyclobutene-containing hydrocarbon. The resulting BCB monomer has ideal curing kinetics for applications benefitting from addition-ring opening orthogonal curing mechanisms, as determined by differential scanning calorimetry (DSC). Further, the monomers can be thermally copolymerized with styrene and other addition polymerizable monomers via thermal free radical polymerization at temperatures that allow for subsequent ring opening cure. Still further, the monomers made by the methods of the present invention are air and benchtop stable solids at room temperature. The resulting copolymers also show thermal stability where other phenoxy resins, such as resorcinol phenoxy BCB have been shown to decompose.

In accordance with the methods of the present invention, deprotection of an organic alkali cleavable protecting group, such as an alkanoyl group, from an addition polymerizable monomer or resin, amine group containing monomer or resin or oligoaromatic compound resin in organic alkali can be followed by reaction with an alpha-halide (α-halide) or strong acid conjugate leaving group containing arylcyclobutene compound as a reducing agent. The deprotection or deacylation reaction is followed by nucleophilic substitution in the same kettle, vessel or pot. In reacting via nucleophilic substitution, the contents of the pot are heated to a temperature of up to 80° C. If the temperature is too high, the materials might autopolymerize or ring open. However, despite the relatively mild temperature of reaction, the monomer yields of methods have heretofore not been attained.

In accordance with the methods of deprotecting or deacylating an oligoaromatic phenol compound containing a phenolic hydroxyl of the present invention, the organic alkali cleavable protecting group is not a phenolic group. Accordingly, the oligoaromatic phenol compound containing a phenolic hydroxyl that results from the deprotecting or deacylating includes one or more phenolic hydroxyl in addition to the hydroxyl group formed by the deprotecting or deacylating.

Preferably, to prevent formation of aldehydes in the product monomer or resin of the present invention, each of the deprotecting and the reacting via nucleophilic substitution is carried out in anhydrous polar media.

In accordance with the present invention, the methods are suitable for making addition polymerizable monomer materials, such as addition polymerizable arylcyclobutene-containing monomers having one or more aryloxy, such as phenoxy, aminophenol, amino oligophenol or oligophenolic groups. The methods in accordance with the present invention are also useful in making arylcyclobutene compounds containing aromatic amine functional groups or oligoaromatic phenol resins. Preferably, the methods of making monomer or resin materials in accordance with the present invention provide addition polymerizable arylcyclobutene compound having one or more aryloxy, such as phenoxy, oligophenolic groups.

In addition, the methods in accordance with the present invention can provide amine containing arylcyclobutene-containing monomers having one or more aryloxy, such as phenoxy, or oligophenolic groups; and the methods in accordance with the present invention can provide novolac or phenolic resin containing arylcyclobutene compounds.

The methods comprise reacting an alpha-halide (α-halide) or strong acid conjugate arylcyclobutene-containing compound, such as a 1-bromo benzocyclobutene (α Br BCB), with a phenol or an oligophenol containing an amine functional group, an addition polymerizable group, such as vinyl phenol, or an oligophenol containing compound, such as a phenolic resin. The phenol or oligophenol is itself formed by deprotecting an addition polymerizable aromatic monomer, aromatic amine containing monomer or oligoaromatic compound containing an organic alkali cleavable protecting group, such as acetoxystyrene or acetoxyaniline.

Preferably, the monomer composition of the present invention may comprise a monomer B having the Structure B, below:

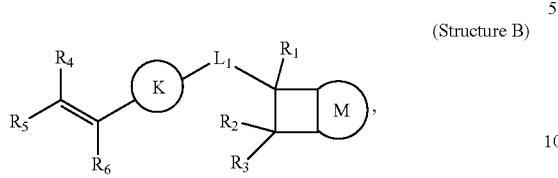

(Structure B)

wherein K is a divalent group chosen from a divalent aryloxy group having from 1 to 10, or, preferably, from 1 to 6 aryl or phenol rings, or, preferably, from 1 to 6 aryl or phenol rings, or an oligophenolic group having from 1 to 10, r, preferably, from 1 to 6 phenol units;

M is a divalent aromatic group chosen from a $C_1$ to $C_6$ alkyl substituted or unsubstituted aromatic radical group, or a $C_1$ to $C_6$ alkyl substituted or unsubstituted divalent heteroaromatic radical group;

$L_1$ is a covalent bond; and, $R_1$ through $R_6$ are each independently selected from a monovalent group chosen from hydrogen, deuterium, halide, hydroxyl, a $C_1$ to $C_6$ alkyl group, a $C_1$ to $C_6$ alkoxy group, a $C_1$ to $C_6$ alkyl substituted hydrocarbon group, a heteroatom containing hydrocarbon group, a $C_1$ to $C_6$ alkyl substituted heterohydrocarbon group, a cyano group, or an hydroxyl group, or preferably, each of $R_1$, $R_2$ and $R_3$ is a hydrogen, or, more preferably, each of $R_1$ through $R_6$ is a hydrogen.

Preferably, the methods of the present invention provide a monomer composition, such as one comprising vinyl phenoxy BCB in which the polymerizable group is connected the four membered BCB ring, as shown in formula I, below. The monomer is 7-((4-vinylbenzyl)oxy)bicyclo [4.2.0]octa-1(6),2,4-triene. The present invention also enables the provision of a copolymer, such as a styrene-co-vinyl phenoxy BCB.

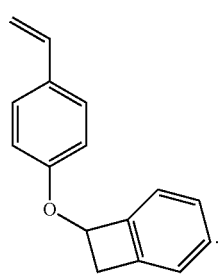

(I)

In accordance with the monomer compositions of the present invention, addition polymerizable monomer mixtures of one or more addition polymerizable arylcyclobutene-containing monomers A having one or more aryloxy, or oligophenolic group, one or more aromatic addition polymerizable second monomers, and, if desired, one or more other addition polymerizable monomers chosen from an addition polymerizable nitrogen heterocycle containing third monomer, an addition polymerizable fourth monomer, or, preferably, both of the one or more third monomers and the one or more fourth monomers.

The monomer compositions are suitable for forming polymers by addition polymerization, such as at temperatures of from ambient temperature to 140° C. The resulting polymers find use in making, for example, thin films, coatings or bulk dielectric materials, which can be dried or soft baked at from 60 to 140° C., followed by ring opening cure at from 140 to 220° C.

EXAMPLES

The present invention will now be described in detail in the following, non-limiting Examples:

Unless otherwise stated all temperatures are room temperature (21-23° C.) and all pressures are atmospheric pressure (~760 mm Hg or 101 kPa).

Notwithstanding other raw materials disclosed below, the following raw materials were used in the Examples:

BCB: benzocyclobutene;
DMF: dimethylformamide;
THF: tetrahydrofuran; and,
V601: A diazo radical initiator, dimethyl 2,2'-azobis(2-methylpropionate) (CAS No 2589-57-3, Wako Chemical, Japan).

Example 1: Preparation of Vinyl Phenyl Benzocyclobutene

In the following example, as shown by the equation, below a Grignard reagent undergoes a catalyst mediated coupling to a palladium intermediate to form vinylphenyl BCB in a poor yield.

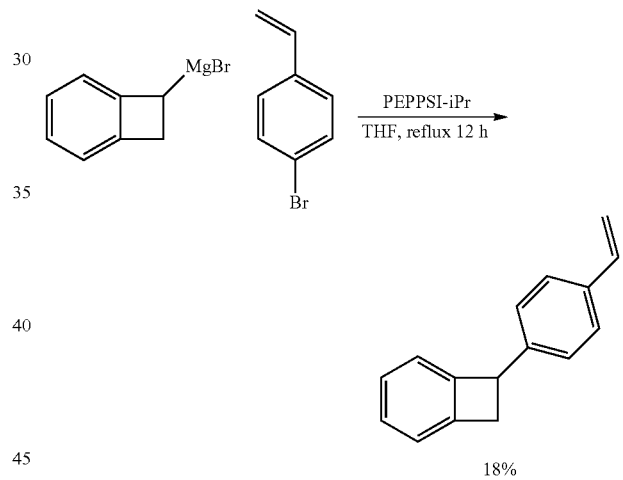

Magnesium turnings (210 mg), sodium hydride (29 mg, 60% oil dispersion) and a magnetic stir bar were added to a 100 ml rbf, capped with a rubber septum and placed under vacuum and allowed to stir for 4 hours. A solution of BrBCB (750 mg) in THF (20 ml) was added via syringe slowly. The solution turned bright yellow and was placed under a nitrogen atmosphere. The solution was left to stir for 30 minutes then added via syringe to a 100 ml rbf containing a stir bar, bromostyrene (1 g), Pd PEPPSI-iPr (1,3-Bis(2,6-Diisopropylphenyl)imidazol-2-ylidene)(3-chloropyridyl) palladium(II) dichloride, CAS no: 905459-27-0) catalyst (190 mg, 5 mol %) and THF (15 ml) under nitrogen and capped with a rubber septum. The mixture turned black after about 30 minutes and was left to stir at room temperature for 12 h. The mixture was added to a separatory funnel containing water (100 ml), and extracted with ethyl acetate (3×100 ml). The combined organics were dried with brine (100 ml) and sodium sulfate, filtered and concentrated in vacuo. The residue was recrystallized in methanol to give the desired product as a colorless solid (203 mg, 18% yield). 1H NMR (500 MHz, Chloroform-d) δ 7.49 (d, J=8.1 Hz, 2H), 7.44-7.26 (m, 6H), 6.84 (dd, J=17.7, 10.8 Hz, 1H), 5.86 (d, J=17.7 Hz, 1H), 5.35 (d, J=10.8 Hz, 1H), 4.86-4.75 (m, 1H), 3.85 (dd, J=13.9, 5.7 Hz, 1H), 3.22 (dd, J=13.9, 2.7 Hz, 1H). A DSC of the resulting monomer showed an exotherm (cure) peak max of 165° C. at a scan rate of 10° C./min.

The yield in the above reaction was very low. Further, no ether linkage resulted from the reaction. However, the cure temperature of the monomer was acceptable.

Example 2: Preparation of Vinyl Phenoxy Benzocyclobutene

In a 250 ml three necked round bottom flask equipped with a polytetraflouroethylene (Teflon™ polymer, Dupont, Wilmington, Del.) coated magnetic stir bar, potassium hydroxide (1.38 g, 1 eq) was dissolved in water (6.83 g). Then 4-acetoxy styrene (4 g, 1 eq) was added dropwise at room temperature, and the solution turned from colorless to pale orange. Potassium carbonate (6.82 g, 2 eq) was added portionwise, and the solution was stirred for one hour. The flask was equipped with a reflux condenser, then 1-bromobenzocyclobutene (4.06 g, 1 eq) was added dropwise in DMF (41 ml). The solution was then heated to 70° C. and allowed to reflux overnight. To the reaction was added water (50 ml) and ethyl acetate (50 ml). The aqueous residue was extracted four times with ethyl acetate (100 ml). The combined organics were extracted with sodium bicarbonate solution (1×100 ml), lithium chloride aqueous solution (1×100 ml) and brine (2×100 ml). The organics were dried over sodium sulfate, filtered and concentrated in vacuo to give the product as a of white solid (3.36 g, 68% yield). Melting point 54-60° C. 1H NMR (600 MHz, Chloroform-d) δ 7.39 (d, J=8.6 Hz, 2H), 7.34 (td, J=7.3, 1.5 Hiz, 1H), 7.31-7.24 (m, 2H), 7.21-7.18 (m, 1H), 6.98 (d, J=8.6 Hz, 2H), 6.69 (dd, J=17.6, 10.9 Hz, 1H), 5.70 (dd, J=4.3, 1.9 Hz, 1H), 5.64 (dd, J=17.6, 0.9 Hz, 1H), 5.15 (dd, J=10.9, 0.9 Hz, 1H), 3.73 (dd, J=14.2, 4.3 Hz, 1H), 3.31 (d, J=14.2 Hz, 1H). 13C NMR (151 MHz, Chloroform-d) δ 157.79, 144.62, 142.57, 136.20, 130.87, 129.93, 127.50, 127.43, 123.48, 123.04, 115.06, 111.80, 74.28, 39.45. Yield from the above example was good and the resulting monomer was a stable solid which has a desirable ring opening cure temperature of 184° C.

Example 3: Preparation of Vinyl Phenoxy Benzocyclobutene

To a 3 L three neck reaction flask fitted with mechanical stirring (300 rpm), a glass additional funnel and a thermocouple was added acetoxystyrene and DMF. The acetoxystyrene was sparged with nitrogen for 15 minutes, then the reactor was submerged in an ice bath to which the thermocouple read 15° C. A solution of sodium methoxide in methanol (NaOMe/MeOH) was fed into the glass addition funnel, and the solution was added portion-wise over 60 minutes, monitoring the exotherm (highest T was 21° C.). When addition was complete, a wine red solution was observed. 1-BrBCB, DMF and a nitroxide containing radical polymerization inhibitor (TEMPO, 2,2,6,6-Tetramethylpiperidine 1-oxyl, CAS 2564-83-2, 25 mg) were fed into the reactor and stirred for 30 minutes. The ice bath was removed and a heating mantle was applied. The mixture was heated to 70° C. (setpoint, never exceeded 70° C.). The mixture was stirred and tracked by NMR (d6 DMSO or d6 acetone) and was complete after 18 h. The solution darkened and a few particulates were observed. The reactor was allowed to cool to 35° C., then 450 ml water was added and stirred for 10 minutes.

The mixture was transferred to a large separation funnel, and organics were dissolved after 6000 ml of a mixture of heptanes had been added with some agitation. The bottom aqueous layer was drained and an NMR was taken to look for remaining organic material, which was not observed.

The organic layer was drained and stripped in vacuo wherein product was placed in 4 glass jars and cycled in vacuum 10 times over 3 days at RT to dry.

The dry product was a tan solid 586.02 g, an excellent 96% yield, 99% purity by UPLC. The. Melting point and NMR spectra of the resulting monomer, 4-vinylphenoxy BCB, matched the product isolated in Example 2, above.

Example 4: Preparation of 4-Amino Phenoxy BCB

In a 250 ml rbf with magnetic stir bar was added aminophenol (1 g, 1 eq), THF (15 ml) and KOtBu (1.23 g, 1.2 eq). The mixture was allowed to stir for 1 hour at room temperature. Bromo BCB (1.68 g, 1 eq) was added in THF (15 ml). The reaction was capped and allowed to stir for 12 h at room temperature. Water (100 ml) was then added. Ethyl acetate (3×100 ml) was used to extract the product from the aqueous phase. The combined organics were dried over sodium sulfate, filtered and concentrated in vacuo. The crude residue was subjected to a column of silica gel using heptanes and ethyl acetate (9:1) as eluent to give product (892 mg, 46%) as a dark oil.

1H NMR (500 MHz, Chloroform-d) δ 7.32 (dt, J=6.6, 4.3 Hz, 1H), 7.28-7.23 (m, 2H), 7.18 (d, J=7.4 Hz, 1H), 6.86 (d, J=9.0 Hz, 2H), 6.69 (d, J=9.0 Hz, 2H), 5.59 (dd, J=4.3, 2.1 Hz, 1H), 3.66 (dd, J=14.1, 4.3 Hz, 1H), 3.46 (br s, 2H), 3.28 (d, J=14.1 Hz, 1H). 13C NMR (126 MHz, Chloroform-d) δ 151.04, 145.18, 142.64, 140.49, 129.73, 127.29, 123.47, 123.00, 116.48, 116.36, 74.89, 39.47. DSC Showed an exotherm peak temperature at 179 C at a scan rate of 10 C/min.

The procedure in Example 2 can be followed to produce the following products from the corresponding unsaturated starting materials shown in the table, below:

| Example | Organic Alkali Cleavable Protecting Group Containing Monomer | Product |
|---|---|---|
| 5 | structure 1 | structure 2 |

| Example | Organic Alkali Cleavable Protecting Group Containing Monomer | Product |
|---|---|---|
| 6 | 3 | 4 |
| 7 | 5 | 6 |

1. Propane-2,2-diylbis(2-allyl-4,1-phenylene) diacetate;
2. 7,7'-((propane-2,2-diylbis(2-allyl-4,-phenylene))bis(oxy))bis(bicyclo[4.2.0]octa-1,3,5-triene);
3. 3, 5-diethynylphenyl acetate;
4. 7-(3,5-diethynylphenoxy)bicyclo[4.2.0]octa-1(6),2,4-triene;
5. 3,3'-diallyl[1,1'-biphenyl]-4,4'-diyl diacetate;
6. 7,7'-((3,3'-diallyl-[1,1'-biphenyl]-4,4'-diyl)bis(oxy))bis(bicyclo[4.2.0]octa-1(6),2,4-triene).

Example 8: Preparation of a Copolymer of Vinyl Phenoxy Benzocyclobutene Co Styrene Styrene (4.77 g) and Vinyl Phenoxy Benzocyclobutene (1.13 g) were dissolved in THF (3.98 g) along with V601™ initiator (70 mg) in an EZ Max™ 100 ml jacketed reactor (Mettler Toledo, Columbia, Md.) equipped with overhead stirring and nitrogen atmosphere. The solution was purged with nitrogen gas for 30 minutes, then heated to an internal temperature of 60° C. overnight. The resulting viscous solution was diluted with THF (20 ml) then precipitated into methanol (250 ml), filtered and dried overnight in vacuo to give the copolymer (4.23 g, 72% yield). Mn 36.6 k, Mw 79.1 k. The polymer curing kinetics were evaluated via differential scanning calorimetry (DSC, TA Instruments Q2000, TA instruments, New Castle, Del.) at a ramp rate of 2, 5, 10 and 20° C./min. The Kissinger method was used to determine a ring opening activation barrier of 24.2 kcal/mol. Thermal stability was evaluated using thermogravimetric analysis (TA Instruments Q5000) under a nitrogen atmosphere, wherein a solid polymer sample was placed in a TGA pan and run out to 400° C. at a rate of 10° C./min.

The TGA of the resulting copolymer exhibited a five percent weight loss value at 300° C.

We claim:
1. A method of making a monomer comprises:
deprotecting or deacylating an organic alkali cleavable protecting group containing aromatic monomer selected from the group consisting of an addition polymerizable group containing aromatic monomer, an amine containing aromatic monomer, and an oligoaromatic phenol compound containing a phenolic hydroxyl by hydrolyzing it to remove the protecting group in organic alkali in a polar solvent containing an excess of alkali $C_1$ to $C_7$ alkoxide to form an hydroxyl functional addition polymerizable aromatic monomer, hydroxyl functional aromatic amine functional group containing monomer or hydroxyl functional oligoaromatic compound, followed by;
reacting via nucleophilic substitution the resulting hydroxyl functional addition polymerizable aromatic monomer, aromatic amine functional group containing aromatic monomer or oligoaromatic compound with an alpha-halide (α-halide) or strong acid conjugate leaving group containing arylcyclobutene compound in a polar solvent, to yield an arylcyclobutene-containing addition polymerizable aromatic monomer, aromatic amine containing monomer or oligoaromatic phenol resin having an ether linkage from the cyclobutene ring to an aromatic group of the addition polymerizable aromatic monomer aromatic amine or oligoaromatic phenol.

2. The method as claimed in claim 1, wherein the organic alkali cleavable protecting group in the organic alkali cleavable protecting group containing addition polymerizable aromatic monomer, amine functional group containing aromatic monomer or oligoaromatic phenol compound containing a phenolic hydroxyl is chosen from a $C_2$ to $C_9$ alkanoyl group or an alkyl carbonate group.

3. The method as claimed in claim 2, wherein, the addition polymerizable aromatic monomer, amine containing aromatic monomer or oligoaromatic phenol compound containing an organic alkali cleavable protecting group is acetoxystyrene.

4. The method as claimed in claim 1, wherein in the hydrolyzing, the organic alkali is a $C_1$ to $C_4$ alkoxide.

5. The method as claimed in claim 1, wherein the alpha-halide (α-halide) or strong acid conjugate leaving group containing arylcyclobutene compound has a bromide on the cyclobutene ring.

6. The method as claimed in claim 1, wherein the reacting via nucleophilic substitution comprises heating the hydroxyl functional addition polymerizable aromatic monomer, hydroxyl functional aromatic amine functional group containing monomer or hydroxyl functional oligaromatic phenol compound with the alpha-halide (α-halide) or strong acid conjugate leaving group containing arylcyclobutene compound in the organic alkali in the polar solvent at a temperature of from 55 to 80° C.

7. The method as claimed in claim 6, wherein the reacting takes place in the presence of a free radical inhibitor.

8. The method as claimed in claim 1, wherein the hydroxyl functional addition polymerizable aromatic monomer, hydroxyl functional aromatic amine functional group containing monomer or hydroxyl functional oligoaromatic phenol compound formed by deprotecting or deacylating is selected from the group consisting of a vinylphenol; an allyl phenol; an alkynyl phenol; a vinyl oligophenol; a vinyl naphthol; a vinylphenol having multiple vinyl groups; a vinylphenol having multiple vinyl groups and multiple aromatic rings; an allyloligophenol having from 2 to 10 aromatic rings or phenolic rings; an alkynyl oligophenol having from 2 to 10 aromatic rings or phenolic rings; an aminophenol; an amino oligophenol; and an oligoaromatic phenol containing the hydroxyl functional group and a phenolic hydroxyl.

9. The method as claimed in claim 1, wherein when the hydroxyl functional addition polymerizable aromatic monomer, hydroxyl functional aromatic amine or hydroxyl functional oligoaromatic phenol formed by deprotecting or deacylating comprises a vinyl oligophenol having from 2 to 10 aromatic rings or phenolic rings, an aminophenol, an amino oligophenol or any oligoaromatic phenol, it is substantially free of aldehydes.

10. The method as claimed in claim 1, further comprising:
purifying the arylcyclobutene-containing addition polymerizable aromatic monomer, aromatic amine functional group containing monomer or oligoaromatic phenol having an ether linkage from the cyclobutene ring to an aromatic group of the addition polymerizable aromatic monomer, aromatic amine functional group containing monomer or oligoaromatic phenol.

* * * * *